United States Patent
Esposito et al.

(10) Patent No.: US 10,190,954 B2
(45) Date of Patent: Jan. 29, 2019

(54) PRE-STRAINED COMPOSITE TEST COUPONS

(71) Applicant: The Boeing Company, Chicago, IL (US)

(72) Inventors: Jack J. Esposito, Auburn, WA (US); Samuel J. Tucker, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 167 days.

(21) Appl. No.: 14/727,236

(22) Filed: Jun. 1, 2015

(65) Prior Publication Data

US 2016/0349160 A1    Dec. 1, 2016

(51) Int. Cl.
*G01N 3/08* (2006.01)
*G01N 3/18* (2006.01)
(Continued)

(52) U.S. Cl.
CPC ............... *G01N 3/18* (2013.01); *G01N 3/08* (2013.01); *B29C 66/721* (2013.01); *B29C 66/7212* (2013.01); *B29C 70/202* (2013.01); *B29C 70/207* (2013.01); *B29C 70/228* (2013.01); *B29C 70/30* (2013.01); *G01N 2203/006* (2013.01); *G01N 2203/0017* (2013.01); *G01N 2203/0062* (2013.01);
(Continued)

(58) Field of Classification Search
CPC . B29C 66/7212; B29C 66/721; B29C 70/202; B29C 70/228; B29C 70/207; B29C 70/30; G01N 3/08; G01N 2203/0017; G01N 2203/0208; G01N 2203/028; G01N 2203/0091; G01N 2203/006; G01N 2203/0075; G01N 2203/0252; G01N 2203/0282; G01N 2291/0231; G01N 2291/0258
USPC ......... 73/826, 827, 833, 834, 788, 799, 789, 73/802
See application file for complete search history.

(56) References Cited

U.S. PATENT DOCUMENTS 4,031,746 A * 6/1977 Furuta .................... G01N 3/068
                                                              702/43
4,368,234 A * 1/1983 Palmer .................. B29C 70/202
                                                              139/426 R
(Continued)

OTHER PUBLICATIONS

Dey et al. "Natural frequencies of delaminated composite rotating conical shells—A finite element approach" Finite Elements in Analysis and Design, vol. 56, Sep. 2012, pp. 41-51. Accessed [Online] Mar. 24, 2017 <http://www.sciencedirect.com/science/article/pii/S0168874X12000315>.*

(Continued)

*Primary Examiner* — Jonathan Dunlap
(74) *Attorney, Agent, or Firm* — Toler Law Group, P.C.

(57) ABSTRACT

A composite test coupon includes a plurality of plies. The plurality of plies include first ply layers and second ply layers. The first ply layers have first fibers and a substantially uniform matrix material associated with the first fibers. The second ply layers have second fibers and a pre-stressed matrix material associated with the second fibers. The first fibers are oriented in a first direction, and the second fibers are oriented in a second direction that is different from the first direction. The pre-stressed matrix material includes stress induced cracks between the second fibers of each of the second ply layers.

18 Claims, 6 Drawing Sheets

(51) Int. Cl.
  *B29C 70/30* (2006.01)
  *B29C 65/00* (2006.01)
  *B29C 70/20* (2006.01)
  *B29C 70/22* (2006.01)

(52) U.S. Cl.
  CPC ............... *G01N 2203/0073* (2013.01); *G01N 2203/0075* (2013.01); *G01N 2203/0091* (2013.01); *G01N 2203/0096* (2013.01); *G01N 2203/028* (2013.01); *G01N 2203/0208* (2013.01); *G01N 2203/0252* (2013.01); *G01N 2203/0282* (2013.01); *G01N 2203/0298* (2013.01); *G01N 2291/0231* (2013.01); *G01N 2291/0258* (2013.01)

(56) References Cited

U.S. PATENT DOCUMENTS

| | | | | |
|---|---|---|---|---|
| 5,083,465 | A * | 1/1992 | Myers | G01B 5/30 |
| | | | | 33/790 |
| 5,305,645 | A * | 4/1994 | Reifsnider | G01N 3/32 |
| | | | | 73/808 |
| 5,866,272 | A * | 2/1999 | Westre | B32B 3/12 |
| | | | | 244/119 |
| 5,918,284 | A * | 6/1999 | Blanch | A61B 17/06004 |
| | | | | 73/827 |
| 6,176,142 | B1 * | 1/2001 | Ericson | G01N 3/04 |
| | | | | 73/856 |
| 6,370,962 | B1 * | 4/2002 | Sullivan | G01N 3/08 |
| | | | | 73/826 |
| 6,880,385 | B2 * | 4/2005 | Esser | G01N 3/08 |
| | | | | 73/826 |
| 8,201,371 | B2 * | 6/2012 | Kismarton | B29C 65/08 |
| | | | | 248/188.2 |
| 8,286,498 | B1 * | 10/2012 | Robertson | G01N 3/08 |
| | | | | 73/826 |
| 8,324,017 | B2 | 12/2012 | Han | |
| 8,342,017 | B1 * | 1/2013 | Bossi | G01N 19/04 |
| | | | | 73/150 A |
| 8,720,825 | B2 * | 5/2014 | Kismarton | B29C 65/562 |
| | | | | 244/129.1 |
| 9,108,366 | B2 * | 8/2015 | Pulnikov | B29C 70/56 |
| 9,347,868 | B2 * | 5/2016 | Van Voast | G01N 19/04 |
| 2003/0188585 | A1 * | 10/2003 | Esser | G01N 3/08 |
| | | | | 73/826 |
| 2005/0217388 | A1 * | 10/2005 | Heyman | G01N 3/32 |
| | | | | 73/827 |
| 2006/0070452 | A1 | 4/2006 | Bohlmann et al. | |
| 2010/0219294 | A1 * | 9/2010 | Kismarton | B29C 65/08 |
| | | | | 244/119 |
| 2011/0045232 | A1 * | 2/2011 | Kismarton | B29C 65/562 |
| | | | | 428/113 |
| 2014/0234571 | A1 | 8/2014 | Lee et al. | |
| 2014/0299259 | A1 * | 10/2014 | Pulnikov | B29C 70/56 |
| | | | | 156/162 |
| 2014/0326074 | A1 | 11/2014 | Van Voast et al. | |
| 2014/0333758 | A1 | 11/2014 | Wu et al. | |
| 2014/0352451 | A1 * | 12/2014 | Kismarton | G01N 3/02 |
| | | | | 73/826 |
| 2014/0352452 | A1 * | 12/2014 | Jain | G01N 3/066 |
| | | | | 73/834 |
| 2016/0047723 | A1 * | 2/2016 | Esposito | G01N 3/08 |
| | | | | 73/818 |
| 2016/0139016 | A1 * | 5/2016 | Kismarton | G01N 3/08 |
| | | | | 703/1 |

OTHER PUBLICATIONS

Hahn et al. "The Effect of Preloading on Fatigue Damage in Composite Structures: Part I" Department of Transportation—Federal Aviation Administration Technical Report. Apr. 1996 Accessed [Online] Mar. 24, 2017 <http://www.tc.faa.gov/its/worldpac/techrpt/ar95-79.pdf>.*

Choi et al. "Effect of Load Rate on Ultimate Tensile Strength of Ceramic Matrix Composites at Elevated Temperatures" NASA Technical Report. Nov. 1, 2011. Accessed [Online] Mar. 24, 2017 <https://ntrs.nasa.gov/search.jsp?R=20020012646>.*

Gyekenyesi et al. "High Tmperature Tensile Tesitng of Ceramic Composites" NASA Contractor Report 180888. Feb. 1988. Accessed [Online] Mar. 24, 2017 <https://ntrs.nasa.gov/archive/nasa/casi.ntrs.nasa.gov/19880006614.pdf>.*

Nettles, A.T. "Basic Mechanics of Laminated Composite Plates" NASA Reference Publication 1351. Oct. 1994. Accessed [Online] Mar. 24, 2017 <https://ntrs.nasa.gov/archive/nasa/casi.ntrs.nasa.gov/19950009349.pdf>.*

Tarpani et al. "Mechanical Performance of Carbon-epoxy Laminates Part II: Quasi-static and Fatigue Tensile Properties" Materials Research, vol. 9, No. 2, 121-130, 2006. <http://www.scielo.br/pdf/mr/v9n2/29605.pdf>.*

Smith et al. "A Comparison of Transverse Cracking Phenomena in (0/90)s and (90/0)s CFRP Laminates" Applied Composite Materials, vol. 5, pp. 11-23, 1998. <https://link.springer.com/article/10.1023/A:1008847528988>.*

Adams et al. "Tabbing Guide for Composite Test Specimens" DOT/FAA/AR-02/106 Final Report, Oct. 2002 <http://www.tc.faa.gov/its/worldpac/techrpt/ar02-106.pdf>.*

Lorenzo et al. "Damage Assessment by Acousto-Ultrasonic Technique in Composites" Composite Materials: Testing and Design (Eighth Conference), ASTM STP 972, pp. 380-397, 1988 <https://compass.astm.org/DIGITAL_LIBRARY/STP/PAGES/STP26147S.htm>.*

Morscher. "Modal acoustic emission of damage accumulation in a woven SiC/SiC composite". Composites Science and Technology vol. 59, 1999, pp. 687-697.*

Leong et al. "An Investigation of damage accumulation in cross-ply glass/epoxy laminates" Joint FEFG/ICF International Conference on Fracture of Engineering Materials and Structures, Aug. 1991, 251-256.*

Extended European Search Report for EP application No. 16169399.9-1553, dated Oct. 4, 2016, 9 pp.

Designation: D 3039/D 3039M-00, Standard Test Method for Tensile Properties of Polymer Matrix Composite Materials; Published Jul. 2000, Copyright ASTM International,100 Barr Harbor Drive, PO Box C700, West Conshohocken, PA 19426•2959, United States, (12 pgs).

Joyce, P., "Common Lay-up Terms and Conditions," https://www.google.com/search?q=common+lay-up+Terms+and+conditions&ie=utf-8&oe=utf-8&client=firefox-b-1-ab> retrieved Oct. 17, 2018, 14 pgs.

* cited by examiner

PRE-STRAINED COMPOSITE TEST COUPONS

FIELD OF THE DISCLOSURE

The present disclosure is generally related to pre-strained composite test coupons.

BACKGROUND

Some test methods for determination of strength and modulus of a composite laminate material may undervalue a material capability of particular portions of the composite laminate material. Further, some test methods may not provide consistent results at various test conditions.

SUMMARY

In a particular embodiment, a composite test coupon is disclosed that includes a plurality of plies. The plurality of plies include first ply layers and second ply layers. The first ply layers have first fibers and a substantially uniform matrix material associated with the first fibers. The second ply layers have second fibers and a pre-stressed matrix material associated with the second fibers. The first fibers are oriented in a first direction, and the second fibers are oriented in a second direction that is different from the first direction. The pre-stressed matrix material includes stress induced cracks between the second fibers of each of the second ply layers.

In another particular embodiment, a method includes inserting a test coupon of a composite material into a testing device and performing loading operations on the test coupon. The test coupon has a plurality of layers, and the testing device has a first element to secure the test coupon and a second element to secure the test coupon. The plurality of layers of the test coupon are arranged in a cross-ply layup that includes first ply layers and second ply layers. The first ply layers have first fibers and a first matrix material associated with the first fibers, with the first fibers oriented in a first direction. The second ply layers have second fibers and a second matrix material associated with the second fibers, with the second fibers oriented in a second direction that is different from the first direction. The method includes performing a first loading operation on the test coupon. The first loading operation includes applying a first tensile load oriented in the first direction, with the first tensile load corresponding to a threshold load that is less than a failure load. After performing the first loading operation, the method further includes performing a second loading operation on the test coupon. The second loading operation includes increasing tensile loading of the test coupon to the failure load.

In another particular embodiment, a system includes a processor and a memory in communication with the processor. The memory includes instructions that are executable by the processor to perform various operations. The operations include communicating with a testing device that is configured to perform load testing operations on a test coupon of a composite material having a plurality of layers. The plurality of layers of the test coupon are arranged in a cross-ply layup including first ply layers and second ply layers. The first ply layers have first fibers and a first matrix material associated with the first fibers, with the first fibers oriented in a first direction. The second ply layers have second fibers and a second matrix material associated with the second fibers. The second fibers are oriented in a second direction that is different than the first direction. The operations also include sending a first set of instructions to the testing device to perform a first loading operation on the test coupon. The first loading operation includes applying a first tensile load oriented in the first direction, with the first tensile load corresponding to a threshold load that is less than a failure load. The operations further include sending a second set of instructions to the testing device to perform a second loading operation on the test coupon. The second loading operation includes increasing tensile loading of the test coupon to the failure load.

The features, functions, and advantages that have been described can be achieved independently in various embodiments or may be combined in other embodiments, further details of which are disclosed with reference to the following description and drawings.

DETAILED DESCRIPTION

Figure 1:
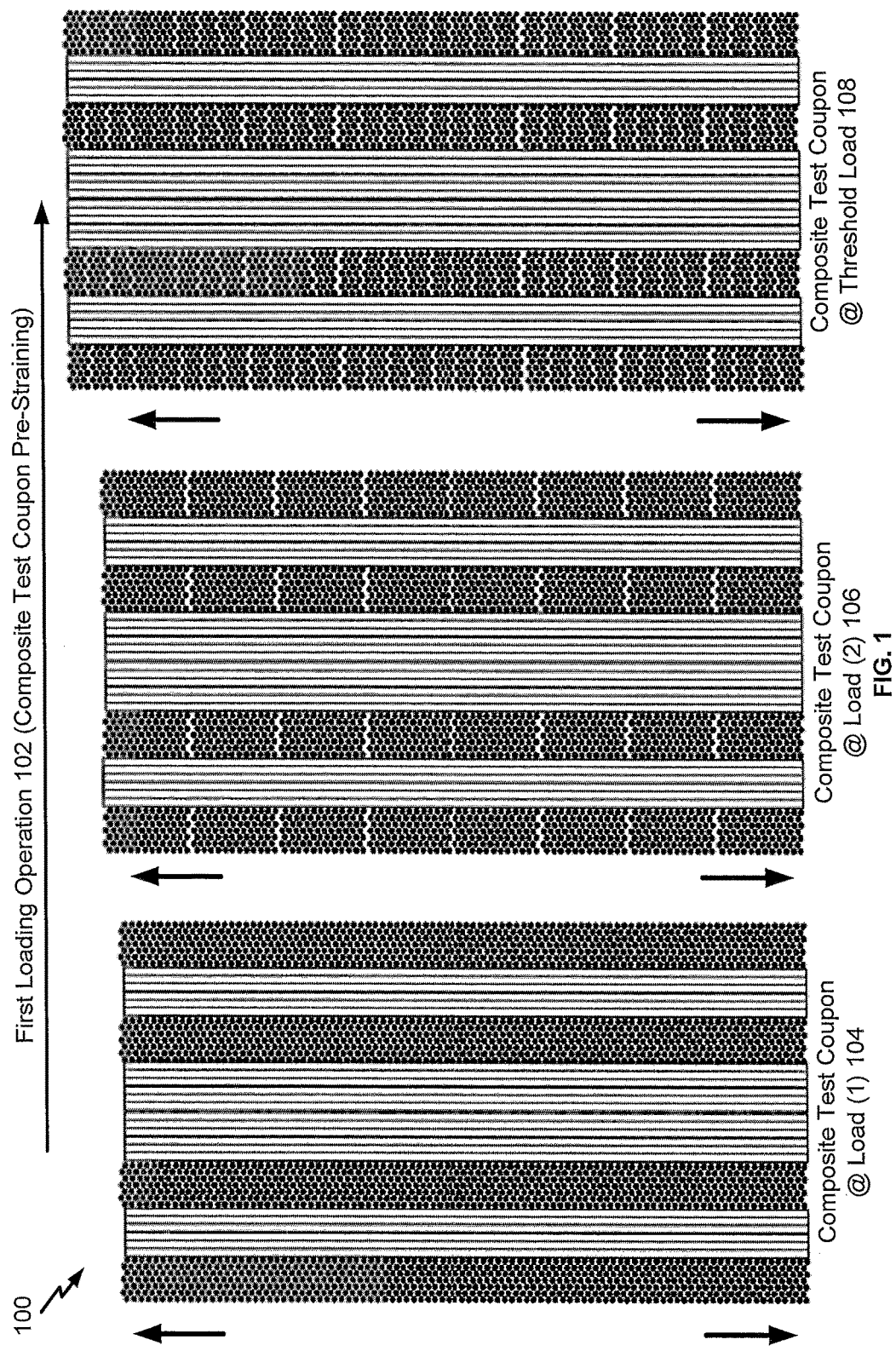
FIG. 1 is a diagram illustrating a test coupon of a composite material during a first loading operation to pre-strain the test coupon by applying a tensile load corresponding to a threshold load that is less than a failure load, according to one embodiment.

The present disclosure describes a test coupon that includes a composite material (also referred to herein as a "composite test coupon") and methods of performing various loading operations on the test coupon. In the present disclosure, the test coupon includes a plurality of layers that are arranged in a cross-ply layup. The cross-ply layup includes first ply layers and second ply layers. The first ply layers have first fibers and a first matrix material associated with the first fibers. The second ply layers have second fibers and a second matrix material associated with the second fibers. The first fibers are oriented in a first direction, and the second fibers are oriented in a second direction that is different from the first direction. A ply layer with fibers oriented in the first direction is also referred to herein as a Zero-Degree ply layer, while a ply layer with fibers oriented in the second direction is also referred to herein as a Ninety-Degree ply layer. The (substantially) zero/ninety degree orientations refer to fiber orientations with respect to a tensile loading direction when performing loading operation(s) on the test coupon. Although zero/ninety degree angles are used to describe directional differences but with fibers of different layers, it will be appreciated that alternative angles between directions are also contemplated, such as 30 degree angles or 45 degree angles, among other alternatives.

In the present disclosure, a test coupon may be "pre-strained" by performing a first loading operation on the test coupon. The first loading operation includes applying a first tensile load oriented in the first direction (corresponding to fiber orientation in the Zero-Degree ply layers), with the first tensile load corresponding to a threshold load that is less than a failure load. The application of the first tensile load to the second matrix material (associated with the Ninety-Degree ply layers) may result in a pre-stressed matrix material that includes stress induced cracks between fibers of each of the Ninety-Degree ply layers. After performing the first loading operation, a second loading operation may be performed in order to calculate strength/modulus value(s) for the Zero-Degree ply layers. Further, surface area of the test coupon that is associated with the Ninety-Degree ply layers may allow loading operations to be performed without applying adhesive tabs to the composite test coupon. As adhesives may degrade under some testing conditions (e.g., high temperature and/or high humidity conditions), the composite test coupon of the present disclosure may allow for "harsh environment" load testing operations to be performed.

Unlike test methods for "unidirectional" test coupons that may under-value a material capability and may not offer consistent results at various test conditions, the test coupon(s) and test method(s) of the present disclosure may allow a test coupon to be used to determine both ultimate strength and (elastic tensile) modulus from zero to failure strain under a variety of test conditions. The test coupon(s) of the present disclosure may reduce a number of tests to be performed in order to characterize a composite material at ply level and may improve accuracy of calculated material strength values.

Further, "unidirectional" coupons may also be susceptible to damage at the ends of the coupons from test machine grips. To prevent such grip damage, adhesives may be used to bond fiberglass tabs to the ends of the "unidirectional" test coupons. However, the use of such adhesives may not allow for accurate testing at elevated temperature with wet conditioned coupons, as the bond is likely to fail before the coupon ultimate strength is reached under such conditions. Additionally, the process of bonding is expensive and time-consuming, and tab quality is inconsistent (being heavily influenced by the skill of the person bonding the tabs).

The cross-ply layup of the test coupon of the present disclosure may include outer plies (at substantially 90 degrees) that may protect load carrying inner plies (at substantially 0 degrees) from damage from the test machine grips. The outer plies (along with friction pads, in some cases) may allow the composite test coupons of the present disclosure to be tested without the use of adhesive tabs, allowing for more accurate testing of specimens under elevated temperature/humidity conditions. The outer plies (at substantially 90 degrees) may also transversely support the load-carrying inner plies (at substantially 0 degrees) and suppress transverse splitting in the test coupon before a fiber direction strength failure. An elastic modulus calculation may be updated to remove a contribution of the outer plies.

As an illustrative example of a test method, the test coupon of the present disclosure may be loaded to a threshold load (e.g., about 90 percent of an expected ultimate failure load), allowing a matrix material in the outer plies to crack and eliminating load transfer between fibers in the outer plies. The test coupon may then be unloaded (e.g., to approximately zero pounds), and the test coupon may then be reloaded at an original load rate until ultimate failure is achieved. Coupon strain data may be recorded during the testing process. The final failure stress and elastic modulus may be attributed to the inner plies and may be calculated accordingly (e.g., based on nominal thickness of ply area associated with the Zero-Degree plies). Elastic modulus equations may be applied over the range of sampled points, and values may be averaged between replicates at each strain interval. A curve may be fit to the averaged data in order to provide a second order polynomial equation. Thus, rather than determining a tensile elastic modulus at a single strain, the second order polynomial equation describes a nonlinear relationship between elastic modulus and strain for a range of strain values.

Referring to FIG. 1, a diagram 100 illustrates a particular embodiment of a loading operation to pre-strain a test coupon that includes a composite material. While not shown in FIG. 1, a testing device (e.g., an extensometer, as shown in FIG. 3) may be used to perform various loading operations on test coupon(s).

FIG. 1 illustrates a test coupon of a composite material at various stages during application of various loads to the test coupon as part of a first loading operation 102. The test coupon includes a plurality of layers arranged in a cross-ply layup. The cross-ply layup includes first ply layers having first fibers and a first matrix material associated with the first fibers. The cross-ply layup also includes second ply layers having second fibers and a second matrix material associated with the second fibers. The first fibers are oriented in a first direction (e.g., along a length of a page when the test coupon is oriented as shown in FIG. 1), and the second fibers are oriented in a second direction that is different than the first direction (e.g., into and/or out of the page when the test coupon is oriented as shown in FIG. 1).

Figure 2:
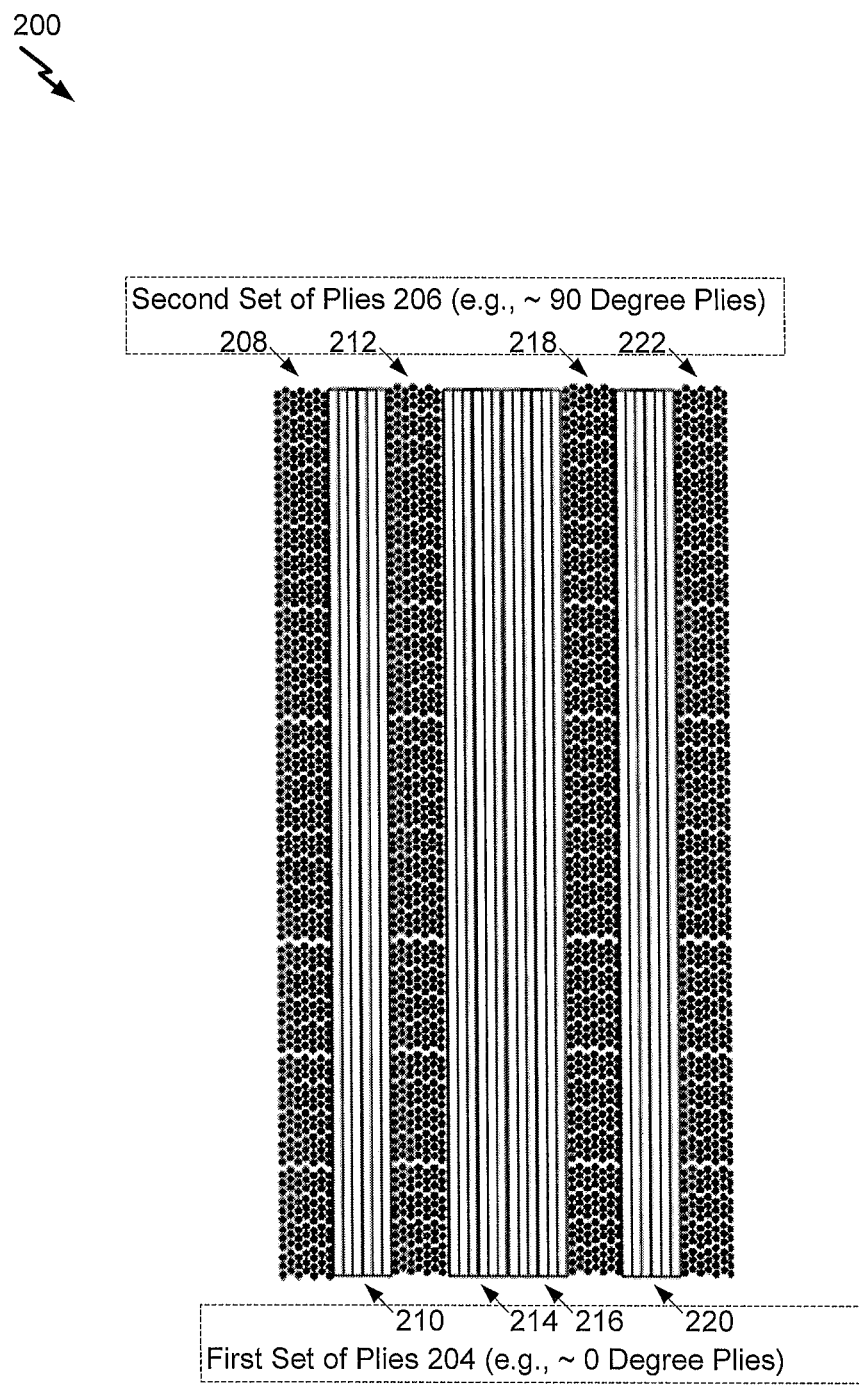
FIG. 2 is a diagram illustrating a composite test coupon after the first loading operation (e.g., a "pre-strained" composite test coupon), according to one embodiment.
Figure 3:
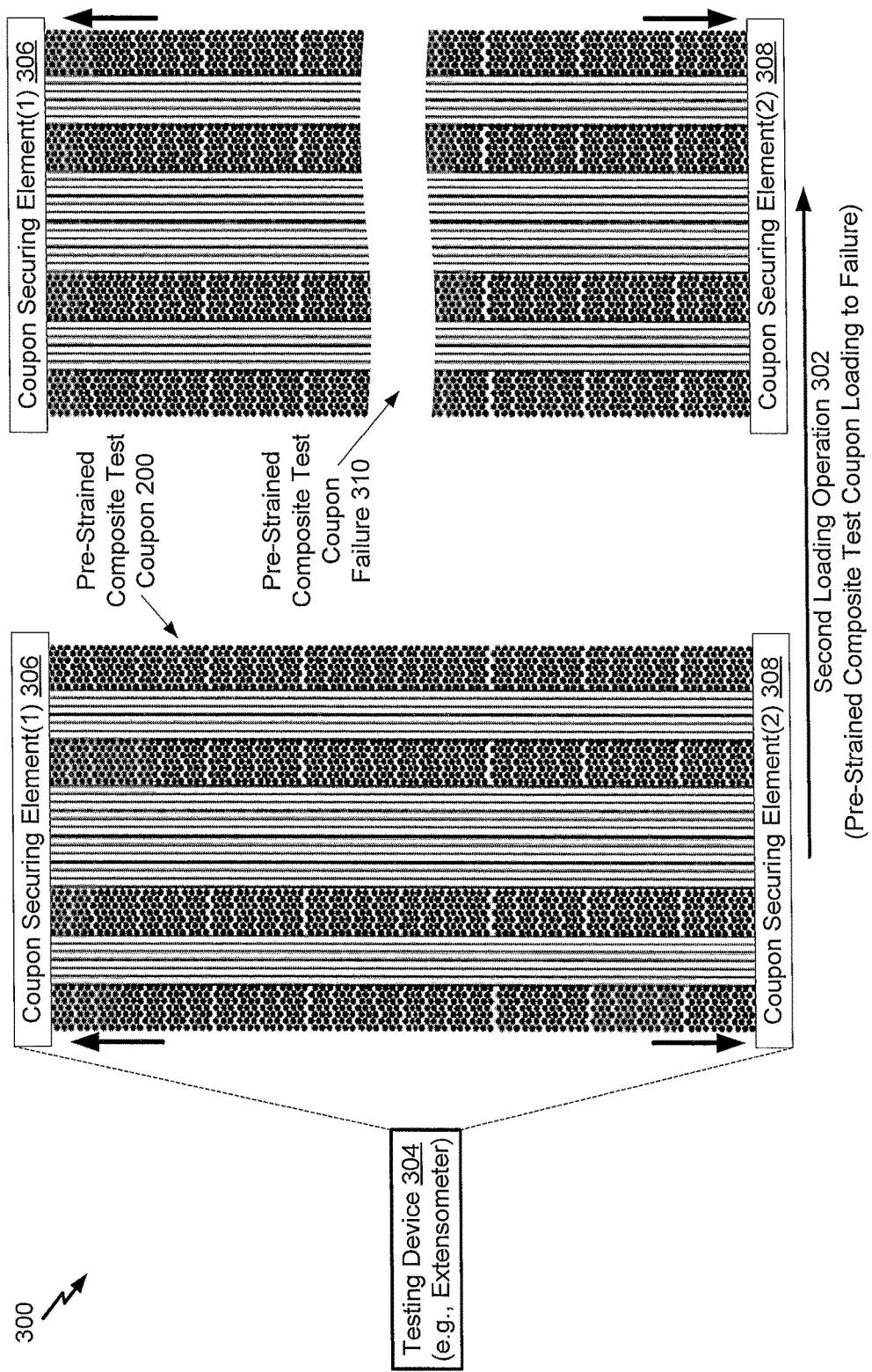
FIG. 3 is a diagram illustrating a second loading operation that includes increasing tensile loading of a pre-strained composite test coupon to a failure load, according to one embodiment.

The first loading operation 102 may be used to form a "pre-strained" composite test coupon for subsequent testing, as described further herein with respect to FIGS. 2 and 3. In the particular embodiment illustrated in FIG. 1, a result of application of a first load (e.g., about 25 percent of a failure load) to the test coupon is illustrated at 104. A result of application of a second load (e.g., about 50 percent of the failure load) to the test coupon is illustrated at 106. A result of application of a third load (e.g., a threshold load that is less than the failure load, such as about 90 percent of the failure load) to the test coupon is illustrated at 108. While not shown in FIG. 1, after loading the test coupon to the threshold load, the tensile load on the test coupon may be reduced (e.g., to substantially zero), as shown in the example graph of FIG. 4. The resulting test coupon is also referred to herein as a "pre-strained" test coupon, as illustrated and further described herein with respect to FIG. 2.

In some cases, a substantially similar "sacrificial" test coupon (e.g., having the same cross-ply layup) may be used to determine an expected failure load. The threshold load may be determined based on the failure load that is measured for the sacrificial test coupon. For example, the threshold load may be in a range of about 85 percent to about 99 percent of the failure load, such as in a range of about 85 percent to about 95 percent of the failure load, in a range of about 87 percent to about 93 percent of the failure load, or in a range of about 89 percent to about 91 percent of the failure load. In a particular embodiment, the threshold load may be about 90 percent of the failure load. In some cases, acoustic testing of a pre-strained test coupon may be used to determine whether a particular threshold load value is indicative of substantial cracks being formed in the matrix material of the second ply layers.

Cracks in the matrix material of the second ply layers may result in a significant reduction in a contribution of the second ply layers to an overall tensile strength of a test coupon. Substantial removal of the contribution of the second ply layers to the overall tensile strength may allow for a more accurate determination of a tensile strength associated with the first ply layers. During subsequent loading operations on a pre-strained test coupon, the second ply layers may provide additional surface area for securing the pre-strained test coupon to a testing device in order to avoid the use of adhesive tabs for securing the test coupon. As adhesive tabs may be subject to degradation under certain conditions (e.g., high temperature and/or high humidity), the ability to secure a test coupon to a testing device without adhesive tabs may allow for load testing operations to be performed under a wide range of conditions (e.g., harsh environment testing). Accordingly, the first loading operation 102 may be performed above a temperature threshold (e.g., associated with adhesive tab de-bonding), above a humidity threshold (e.g., a "wet" environment associated with adhesive tab de-bonding), or a combination thereof.

Thus, FIG. 1 illustrates an example of a first loading operation performed on a test coupon of a composite material that includes a plurality of plies arranged in a cross-ply layup. The application of a threshold load that is less than an expected failure load of a test coupon results in the formation of a pre-strained composite test coupon for subsequent load testing operations, as further described herein.

Referring to FIG. 2, an example of a pre-strained composite test coupon is illustrated and is generally designated 200. In a particular embodiment, the pre-strained composite test coupon 200 of FIG. 2 may correspond to the test coupon of FIG. 1 after application of the threshold load and subsequent reduction of the tensile load (e.g., to substantially zero).

In FIG. 2, the pre-strained composite test coupon 200 includes a plurality of layers that are arranged in a cross-ply layup that includes first ply layers and second ply layers. The first ply layers and the second ply layers have fibers and matrix material(s) associated with the fibers. In some cases, the first ply layers and the second ply layers have substantially similar material compositions. To illustrate, the first ply layers and the second ply layers may be the same material, and the first/second ply layers are "turned" 90 degrees with respect to one another. Thus, for ease of illustration purposes only, FIG. 2 shows a macroscopic view of the pre-strained test coupon 200. As described further herein with respect to FIG. 1, the first loading operation 102 results in stress induced cracks between fibers of each of the second ply layers, as illustrated by the irregularity of the individual second ply layers and voids/spacing between the second ply layers.

The pre-strained test coupon 200 includes first fibers that are oriented in a first direction and second fibers that are oriented in a second direction (that is different from the first direction). A ply having ply layers with fibers oriented in the first direction is also referred to herein as a Zero-Degree ply, while a ply having ply layers with fibers oriented in the second direction is also referred to herein as a Ninety-Degree ply. The (substantially) zero/ninety degree orientations refer to fiber orientations with respect to a tensile loading direction when performing loading operations.

The pre-strained composite test coupon 200 illustrated in FIG. 2 includes a first set of plies 204 associated with the first ply layers and a second set of plies 206 associated with the second ply layers. The first set of plies 204 includes a first number of plies, and the second set of plies 206 includes a second number of plies. FIG. 2 illustrates that, in some cases, the first number of plies may be same as the second number of plies. In a particular embodiment, the first number of plies may include at least two plies (e.g., four plies in FIG. 2), and the second number of plies may include at least two plies (e.g., four plies in FIG. 2).

In the particular embodiment illustrated in FIG. 2, the pre-strained composite test coupon 200 includes eight symmetrically arranged plies. In the example of FIG. 2, the arrangement of plies includes a first ply 208, a second ply 210, a third ply 212, a fourth ply 214, a fifth ply 216, a sixth ply 218, a seventh ply 220, and an eighth ply 222. The second ply 210 (of the first set of plies 204) is disposed adjacent to the first ply 208 (of the second set of plies 206). The third ply 212 (of the second set of plies 206) is disposed adjacent to the second ply 210. The fourth ply 214 (of the first set of plies 204) is disposed adjacent to the third ply 212. The fifth ply 216 (of the first set of plies 204) is disposed adjacent to the fourth ply 214. The sixth ply 218 (of the second set of plies 206) is disposed adjacent to the fifth ply 216. The seventh ply 220 (of the first set of plies 204) is disposed adjacent to the sixth ply 218. The eighth ply 222 (of the second set of plies 206) is disposed adjacent to the seventh ply 220.

As an alternative example of a symmetrical arrangement of plies, a pre-stressed test coupon may include two plies associated with the first set of plies 204 and two plies associated with the second set of plies 206. To illustrate, the first set of plies 204 may include the fourth ply 214 and the fifth ply 216 (without the second ply 210 and the seventh ply 220 shown in FIG. 2), and the second set of plies 206 may include the third ply 212 and the sixth ply 218 (without the first ply 208 and the eighth ply 222 shown in FIG. 2). It will be appreciated that a pre-stressed test coupon may include an alternative number and/or arrangement of plies.

Thus, FIG. 2 illustrates an example of a "pre-strained" composite test coupon that includes a plurality of plies arranged in a cross-ply layup. As described further herein, the first loading operation to pre-stress the second matrix material (associated with the Ninety-Degree ply layers) results in the pre-strained composite test coupon with stress induced cracks in the second matrix material. As described further herein with respect to FIG. 3, a second loading operation that is performed on the pre-strained composite test coupon may provide a more accurate estimate of strength/modulus value(s) for the Zero-Degree ply layers.

FIG. 3 is a diagram 300 that illustrates an example of a second loading operation 302 that includes increasing tensile loading of a test coupon (e.g., the pre-strained composite test coupon 200 of FIG. 2) to a failure load. FIG. 3 illustrates that surface area of the test coupon that is associated with the Ninety-Degree ply layers may allow the second loading operation 302 to be performed without applying adhesive tabs to the test coupon. As adhesives may degrade under some testing conditions (e.g., high temperature and/or high humidity conditions), the second loading operation 302 may correspond to a "harsh environment" load testing operation (in some cases), such as above a temperature threshold (e.g., associated with adhesive tab de-bonding), above a humidity threshold (e.g., a "wet" environment associated with adhesive tab de-bonding), or a combination thereof.

FIG. 3 illustrates that the test coupon 200 may be inserted into a testing device 304 (e.g., an extensometer). The testing device 304 includes a first element 306 to secure the test coupon 200 (identified as "Coupon Securing Element(1)" in FIG. 3) and a second element to secure the test coupon 200 (identified as "Coupon Securing Element(2)" in FIG. 3). As further illustrated in the example of FIG. 2, the test coupon 200 may not include adhesive tabs for securing the test coupon 200 to the first element 306 and the second element 308 of the testing device 304. As adhesive tabs may degrade under some testing conditions (e.g., high temperature/humidity, etc.), securing the test coupon 200 within the testing device 304 without the use of adhesive tabs may allow the second loading operation 302 to be performed above a temperature threshold, above a humidity threshold, or a combination thereof. In some cases, the first element 306 may include a first friction pad to secure a first end of the test coupon 200, and the second element 308 may include a second friction pad to secure a second end of the test coupon 200.

Figure 4:
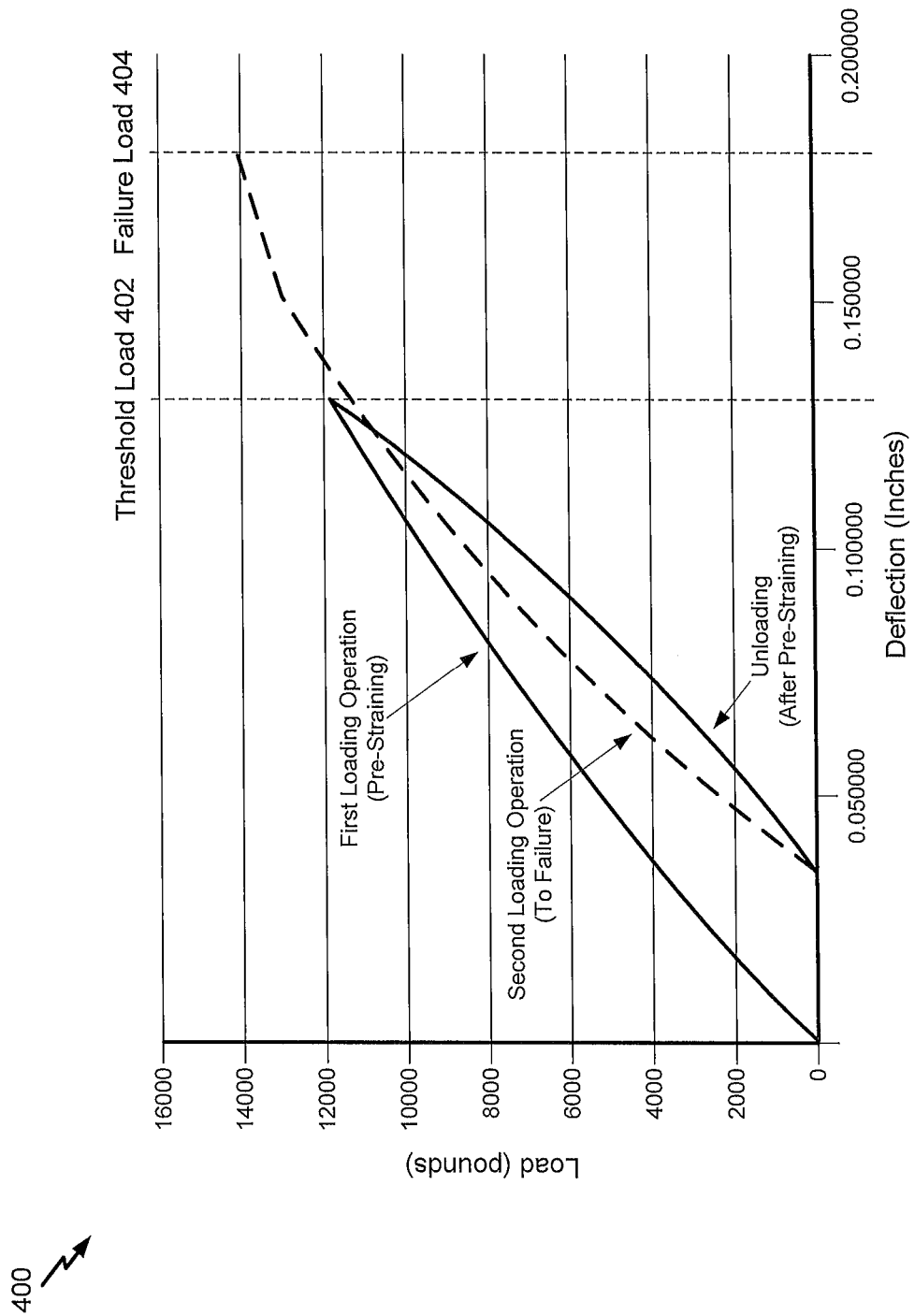
FIG. 4 is a diagram illustrating an example of deflection of a composite test coupon during the first loading operation and the second loading operation, according to one embodiment.

After performing the first loading operation 102 (as illustrated and further described herein with respect to FIG. 1), tensile loading on the test coupon 200 may be reduced (e.g., to substantially zero, as illustrated in the example graph of FIG. 4). The testing device 304 may increase tensile loading on the test coupon 200 to test coupon failure, as shown at 310. The testing device 304 may be configured to measure strain values of the test coupon 200 during tensile loading of the test coupon 200 to the failure load.

In some cases, the testing device 304 (or another computing device) may be configured to calculate one or more modulus values associated with the first ply layers based on the measured strain values. In a particular embodiment, the one or more modulus values may be determined based on nominal thickness values associated with the first ply layers based on the measured strain values. As an illustrative example, referring to FIG. 2, a total nominal thickness value for use in calculating modulus value(s) may be determined based on individual nominal thickness values for each ply layer of the first set of plies 204. To illustrate, the total nominal thickness value may be determined based on nominal thickness values for each ply layer associated with the second ply 210 (of the first set of plies 204), nominal thickness values for each ply layer associated with the fourth ply 214 (of the first set of plies 204), nominal thickness values for each ply layer associated with the fifth ply 216 (of the first set of plies 204), and nominal thickness values for each ply layer associated with the seventh ply 220 (of the first set of plies 204).

While not shown in the example of FIG. 3, in some cases, the testing device 304 may determine the failure load using a sacrificial test coupon. The sacrificial test coupon may have a substantially similar test coupon design (e.g., an "unstressed" test coupon prior to performing the first loading operation 102 illustrated in FIG. 1). The threshold load that is applied during the first loading operation 102 (of FIG. 1) may be determined based on the measured failure load of the sacrificial test coupon. In a particular embodiment, the threshold load may be in a range of about 85 percent to about 99 percent of the failure load, such as in a range of about 85 percent to about 95 percent of the failure load, in a range of about 87 percent to about 93 percent of the failure load, or in a range of about 89 percent to about 91 percent of the failure load.

Thus, FIG. 3 illustrates an example of a second loading operation that includes increasing tensile loading of a pre-strained composite test coupon to a failure load. As described further herein, strength/modulus values associated with the second loading operation may provide a more accurate estimate of strength/modulus value(s) for the Zero-Degree ply layers. Further, in some cases, the second loading operation may be performed under "harsh environment" conditions (e.g., high temperature and/or high humidity conditions) that may correspond to conditions that may be expected for materials that include the Zero-Degree ply layers.

FIG. 4 is a diagram 400 depicting an illustrative, non-limiting example of measured values (e.g., deflection of a composite test coupon) during the first loading operation and the second loading operation, as described further herein with respect to FIG. 1 and FIG. 3. In FIG. 4, the first loading operation (and associated unloading) is illustrated as a solid line, while the second loading operation is illustrated as a dashed line.

In the particular embodiment illustrated in FIG. 4, the solid line illustrates that performing the first loading operation on the test coupon (e.g., as illustrated in FIG. 1) includes increasing tensile loading to a threshold load 402 that is less than a failure load 404. While not shown in FIG. 4, in some cases, the failure load 404 may be determined for a sacrificial test coupon in order to calculate the threshold load 402 to be applied to the test coupon during the first loading operation.

FIG. 4 illustrates a particular example in which the threshold load 402 is about 12,000 pounds, and the failure load 404 is about 14,000 pounds. In this case, the threshold load 402 represents about 86 percent of the failure load 404. However, it will be appreciated that the threshold load 402 may include an alternative load, such as a load in a range of in a range of about 85 percent to about 99 percent of the failure load 404, in a range of about 85 percent to about 95 percent of the failure load 404, in a range of about 87 percent to about 93 percent of the failure load 404, or in a range of about 89 percent to about 91 percent of the failure load 404.

FIG. 4 further illustrates that, after performing the first loading operation, the test coupon may be "unloaded" prior to performing the second loading operation. In the particular embodiment illustrated in FIG. 4, the load on the test coupon is reduced to a tensile load of substantially zero. In some cases, the first loading operation and subsequent unloading operation may result in formation of the pre-strained test coupon 200 of FIG. 2. As illustrated in the example of FIG. 3, the second loading operation (e.g., to the failure load 404 of FIG. 4) may result in failure of the pre-strained test coupon (as shown at 310). As further described herein with respect to FIG. 2, values that are measured during the second loading operation may be used to calculate strength/modulus values for the Zero-Degree ply layers. For example, strength/modulus values for the Zero-Degree ply layers may be calculated based on nominal thickness values for the Zero-Degree ply layers (with the contribution of Ninety-Degree ply layers ignored/removed).

Thus, FIG. 4 illustrates an example of a first loading operation performed on a test coupon that includes a composite material in order to form stress induced cracks in a matrix material associated with the Ninety-Degree ply layers. After performing the first loading operation (and associated unloading operation) to form a pre-strained test coupon, a second loading operation may be performed on the pre-strained test coupon. Values that are measured for the pre-strained test coupon during the second loading operation may be used to calculate strength/modulus values for the Zero-Degree ply layers.

Figure 5:
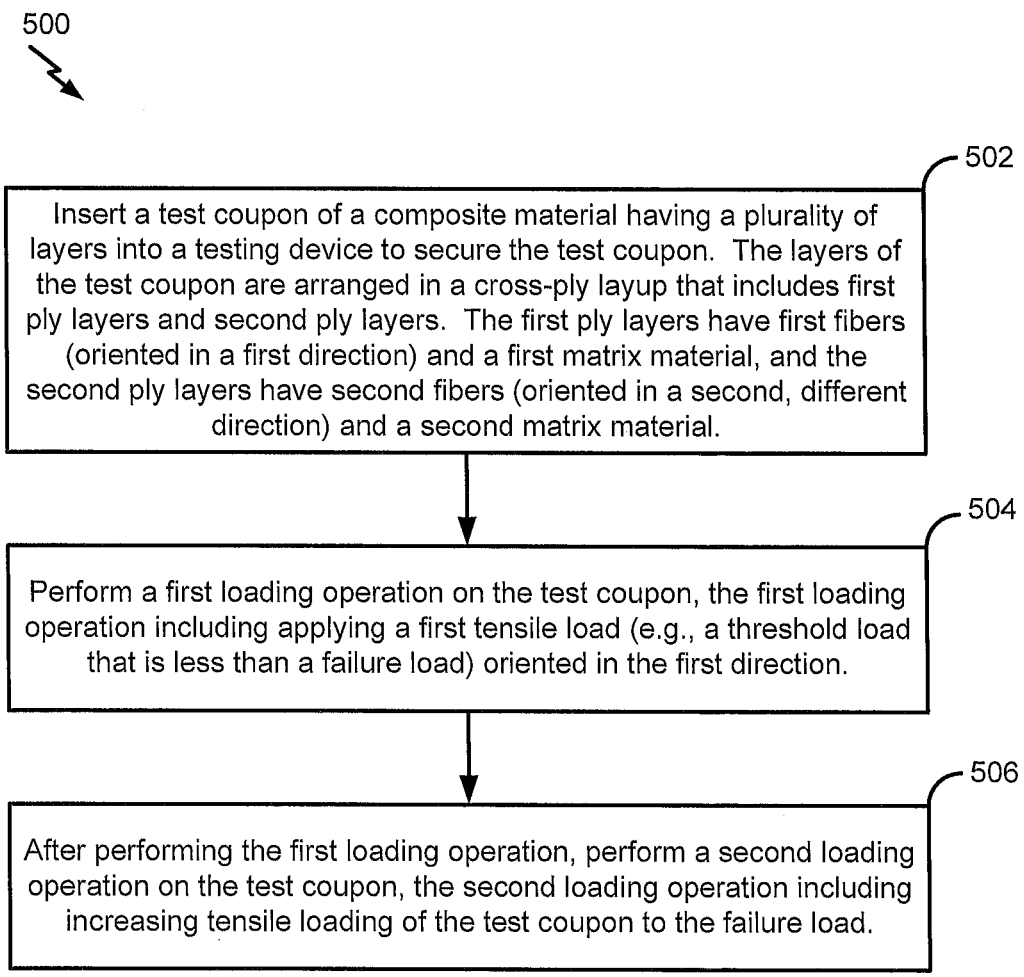
FIG. 5 is a flow chart illustrating a particular embodiment of a method of performing a first loading operation to pre-strain a composite test coupon prior to performing a second loading operation that includes increasing tensile loading of the test coupon to a failure load.

Referring to FIG. 5, a particular embodiment of a method 500 of performing a first loading operation on a test coupon that includes a composite material in order to form a pre-strained composite test coupon prior to performing a second loading operation that includes increasing tensile loading on the pre-strained composite test coupon to a failure load. While not shown in FIG. 5, in some embodiments, a substantially similar sacrificial test coupon may be used to measure a failure load, and the measured failure load may be used to calculate the threshold load to be applied during a first loading operation for another test coupon.

The method 500 includes inserting a test coupon of a composite material having a plurality of layers into a testing device to secure the test coupon, at 502. The layers of the test coupon are arranged in a cross-ply layup that includes first ply layers and second ply layers. The first ply layers have first fibers oriented in a first direction and a first matrix material. The second ply layers have second fibers oriented in a second direction (that is different from the first direction) and a second matrix material. For example, referring to FIG. 3, the testing device 304 may be used to secure an "unstrained" test coupon that includes a composite material. While FIG. 3 illustrates the pre-strained composite test coupon 200 being secured in the testing device 304, it will be appreciated that the testing device 304 of FIG. 3 may be used to secure/load test an unstrained test coupon in order to form the pre-strained test coupon 200 prior to increasing tensile load on the pre-strained test coupon 200 in order to induce test coupon failure (as shown at 310).

The method 500 includes performing a first loading operation on the test coupon, at 504. The first loading operation includes applying a first tensile load (e.g., a threshold load that is less than a failure load) that is oriented in the first direction (e.g., substantially corresponding to an orientation of the Zero-Degree ply layers). For example, referring to FIG. 1, the first loading operation 102 may be performed on an "unstrained" test coupon that includes a composite material. As described further herein, the first loading operation 102 illustrated in FIG. 1 may result in formation of the pre-strained composite test coupon 200 of FIG. 2.

After performing the first loading operation, the method 500 includes performing a second loading operation on the test coupon, at 506. The method 500 may further comprise the step of removing any application of a tensile load to the test coupon or specimen after performing the first loading operation and before performing the second loading operation. The second loading operation includes increasing tensile loading of the test coupon to the failure load. For example, referring to FIG. 3, the second loading operation 302 may performed on the pre-strained test coupon 200. As shown in the example of FIG. 3, the second loading operation 302 may result in test coupon failure, as shown at 310. While not shown in the example of FIG. 5, it will be appreciated that values may be measured while performing the second loading operation on the pre-strained test coupon. The measured values may be used to calculate strength/modulus values for the Zero-Degree ply layers (e.g., based on nominal thickness values).

Thus, FIG. 5 illustrates a particular example of a method of performing a first loading operation on a test coupon that includes a composite material, resulting in stress induced cracks in the Ninety-Degree ply layers. After forming the stress induced cracks, a second loading operation is performed in order to measure values for the pre-strained test coupon. The values that are measured for the pre-strained test coupon may be used to calculate strength/modulus values for the Zero-Degree ply layers. While FIG. 5 illustrates that the first loading operation and the second loading operation are applied to a test coupon, it will be appreciated that one entity may perform the first loading operation (e.g., to form a pre-strained test coupon), while another entity may perform the second loading operation (e.g., applying a tensile load to the pre-strained test coupon to induce failure).

Figure 6:
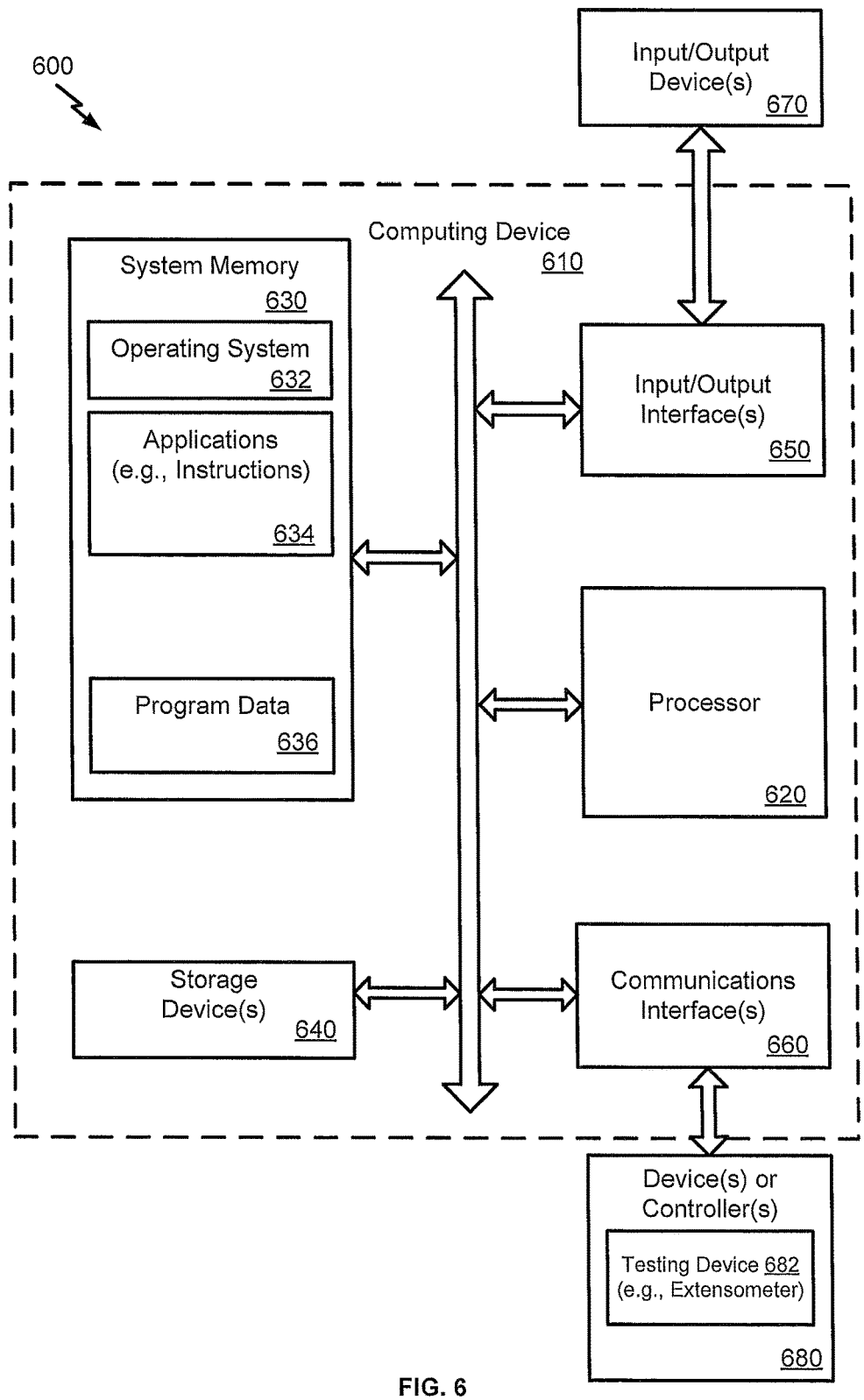
FIG. 6 is an illustration of a block diagram of a computing environment including a general purpose computing device configured to support embodiments of computer-implemented methods and computer-executable program instructions (or code) according to the present disclosure.

FIG. 6 is an illustration of a block diagram of a computing environment 600 including a general purpose computing device 610 configured to support embodiments of computer-implemented methods and computer-executable program instructions (or code) according to the present disclosure. For example, the computing device 610, or portions thereof, may execute instructions to communicate with a testing device 682 to perform loading operation(s) on a test coupon of a composite material. For example, the testing device 682 of FIG. 6 may correspond to the testing device 304 of FIG. 3. The computing device 610, or portions thereof, may further execute instructions according to any of the methods described herein. For example, the computing device 610 may execute instructions according to the method 500 described with respect to FIG. 5.

The computing device 610 may include a processor 620. The processor 620 may communicate with the system memory 630, one or more storage devices 640, one or more input/output interfaces 650, one or more communications interfaces 660, or a combination thereof. The system memory 630 may include volatile memory devices (e.g., random access memory (RAM) devices), nonvolatile memory devices (e.g., read-only memory (ROM) devices, programmable read-only memory, and flash memory), or both. The system memory 630 may include an operating system 632, which may include a basic/input output system for booting the computing device 610 as well as a full operating system to enable the computing device 610 to interact with users, other programs, and other devices. The system memory 630 may include one or more applications 634 which may be executable by the processor 620. For example, the one or more applications 634 may include instructions executable by the processor 620 to perform various operations (e.g., loading operations). Further, the system memory 630 may include program data 636 usable for controlling the testing device 682 to perform the loading operations described herein.

As an example, the application(s) 634 may include instructions executable by the processor 620 to communicate with the testing device 682 that is configured to perform load testing operations on a test coupon of a composite material having a plurality of layers, where the plurality of layers of the test coupon are arranged in a cross-ply layup. As illustrated and further described herein with respect to FIG. 1, prior to performing the first loading operation 102, an "unstressed" test coupon may include first ply layers and second ply layers. The first ply layers have first fibers and a first matrix material associated with the first fibers, and the second ply layers have second fibers and a second matrix material associated with the second fibers. The second fibers are oriented in a second direction that is different than the first direction.

As another example, the application(s) 634 may include instructions executable by the processor 620 to send a first set of instructions to the testing device 682 to perform a first loading operation on a test coupon. As illustrated and further described herein with respect to FIG. 1, the first loading operation may include applying a tensile load oriented in a first direction (of fibers of the first ply layers), with the tensile load corresponding to a threshold load that is less than a failure load.

As a further example, the application(s) 634 may include instructions that are executable by the processor 620 to send a second set of instructions to the testing device 682 to perform a second loading operation on the (pre-stressed) test coupon. As illustrated and further described herein with respect to FIG. 3, the second loading operation may include increasing tensile loading of the (pre-stressed) test coupon to the failure load.

As another example, the application(s) 634 may include instructions executable by the processor 620 to receive, from the testing device 682, strain values of the test coupon during tensile loading of the test coupon to the failure load. The instructions may be further executable by the processor 620 to calculate one or more modulus values associated with the first ply layers based on the measured strain values. As described further herein with respect to FIG. 3, the modulus value(s) may be calculated based on nominal thickness values associated with the first ply layers of the test coupon.

As another example, the application(s) 634 may include instructions executable by the processor 620 to (prior to performing the first loading operation) send a third set of instructions to the testing device 682 to perform a failure load testing operation on a sacrificial test coupon that is substantially similar to the test coupon. The instructions may be further executable by the processor 620 to calculate the threshold load based on information received from the testing device 682 that is associated with the failure load testing operation on the sacrificial test coupon.

The processor 620 may also communicate with one or more storage devices 640. For example, the one or more storage devices 640 may include nonvolatile storage devices, such as magnetic disks, optical disks, or flash memory devices. The storage devices 640 may include both removable and non-removable memory devices. The storage devices 640 may be configured to store an operating system, images of operating systems, applications, and program data. Further, the storage device 640 may be configured to store test values measured by the testing device 682 and/or values that are calculated based on the measured test values (e.g., strength/modulus values for Zero-Degree ply layers). In a particular embodiment, the memory 630, the storage devices 640, or both, include tangible computer-readable media.

The processor 620 may also communicate with one or more input/output interfaces 650 that enable the computing device 610 to communicate with one or more input/output devices 670 to facilitate user interaction. As an example, the computing device 610 may communicate with a display device to display test values that are measured by the testing device 682 and/or values that are calculated based on the measured test values (e.g., strength/modulus values for the Zero-Degree ply layers), among other alternatives. The processor 620 may detect interaction events based on user input received via the input/output interfaces 650. Additionally, the processor 620 may send a display to a display device via the input/output interfaces 650. The processor 620 may communicate with devices or controllers 680 via the one or more communications interfaces 660. For example, the devices or controllers 680 may correspond to the testing device 304 of FIG. 3.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it is to be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
   inserting a test coupon of a composite material having a plurality of layers into a testing device that has a first element to secure the test coupon and a second element to secure the test coupon, wherein the plurality of layers of the test coupon are arranged in a cross-ply layup including:
      inner ply layers having first fibers and a first matrix material associated with the first fibers, the first fibers oriented in a first direction; and
      outer ply layers having second fibers and a second matrix material associated with the second fibers, the outer ply layers including outermost ply layers and the second fibers oriented in a second direction that is different than the first direction;
   performing a first loading operation on the test coupon, wherein the first loading operation includes applying a first tensile load oriented in the first direction, the first tensile load corresponding to a threshold load that is less than a failure load of the first fibers;
   removing the first tensile load after the first tensile load causes cracking along the second direction and between the second fibers of each of the outermost ply layers;
   after removing the first tensile load, performing a second loading operation on the test coupon, wherein the second loading operation includes increasing tensile loading of the test coupon to the failure load of the first fibers;
   receiving, from the testing device, strain values of the test coupon during tensile loading of the test coupon; and determining one or more modulus values associated with a first contribution corresponding to the inner ply layers based on the strain values and based on a nominal thickness of a ply area associated with the inner ply layers, the first contribution independent of a second contribution of the outer ply layers.

2. The method of claim 1, further comprising determining one or more tensile strength values associated with the first contribution corresponding to the inner ply layers based on the nominal thickness of the ply area associated with the inner ply layers.

3. The method of claim 2, wherein the threshold load is greater than ninety percent of the failure load and less than or equal to ninety-nine percent of the failure load.

4. The method of claim 1, wherein the test coupon does not include adhesive tabs for securing the test coupon to the first element and to the second element of the testing device.

5. The method of claim 1, wherein the first loading operation and the second loading operation are performed above a temperature threshold, above a humidity threshold, or a combination thereof.

6. The method of claim 1, further comprising, prior to performing the first loading operation, using the testing device to determine the failure load using a sacrificial test coupon that is substantially similar to the test coupon.

7. The method of claim 1, wherein the threshold load is in a range of about 85 percent to about 99 percent of the failure load.

8. The method of claim 1, wherein the first element of the testing device includes a first friction pad to secure directly to a first end of the test coupon, and wherein the second element of the testing device includes a second friction pad to secure directly to a second end of the test coupon.

9. The method of claim 1, wherein the removing the first tensile load includes completely removing the first tensile load such that the test coupon experiences no tensile load.

10. The method of claim 1, wherein the determining the one or more modulus values is based on a second order polynomial equation, the second order polynomial equation indicating a nonlinear relationship between the one or more modulus values and each strain value of the strain values.

11. The method of claim 1, wherein the first tensile load is less than a second tensile load, the second tensile load less than the failure load of the first fibers, and wherein the first loading operation further comprises:
 applying the second tensile load oriented in the first direction, the second tensile load less than a third tensile load, the third tensile load less than the failure load of the first fibers; and
 applying the third tensile load oriented in the first direction, the third tensile load corresponding to the threshold load.

12. The method of claim 11, wherein the first tensile load is less than or equal to twenty-five percent of the failure load, wherein the second tensile load is greater than twenty-five percent of the failure load and less than or equal to fifty percent of the failure load, and wherein the threshold load is equal to ninety percent of the failure load.

13. The method of claim 1, wherein the threshold load is indicative of a substantial amount of cracks formed in the second matrix material, and further comprising, prior to performing the second loading operation, determining the substantial amount of cracks by performing an acoustic testing operation on the test coupon, wherein the second contribution is based on the substantial amount of cracks, and wherein, in a determination of the one or more modulus values, the second contribution is ignored or the second contribution is removed.

14. A system comprising:
 a processor; and
 a memory in communication with the processor, the memory including instructions executable by the processor to perform operations including:
  communicating with a testing device that is configured to perform load testing operations on a test coupon of a composite material having a plurality of layers, wherein the plurality of layers of the test coupon are arranged in a cross-ply layup including:
   inner ply layers having first fibers and a first matrix material associated with the first fibers, the first fibers oriented in a first direction; and
   outer ply layers having second fibers and a second matrix material associated with the second fibers, the outer ply layers including outermost ply layers and the second fibers oriented in a second direction that is different than the first direction;
  sending a first set of instructions to the testing device to perform a first loading operation on the test coupon, wherein the first loading operation includes applying a first tensile load oriented in the first direction, the first tensile load corresponding to a threshold load that is less than a failure load of the first fibers;
  removing the first tensile load after the first tensile load causes cracking along the second direction and between the second fibers of each of the outermost ply layers, the removing including causing a magnitude of the first tensile load to be zero;
  after removing the first tensile load, sending a second set of instructions to the testing device to perform a second loading operation on the test coupon, wherein the second loading operation includes increasing tensile loading of the test coupon to the failure load of the first fibers;
  receiving, from the testing device, strain values of the test coupon during tensile loading of the test coupon to the failure load; and
  calculating one or more modulus values associated with a first contribution corresponding to the inner ply layers based on the strain values and based on a nominal thickness of a ply area associated with the inner ply layers, the first contribution independent of a second contribution associated with the outer ply layers.

15. The system of claim 14, wherein the threshold load is greater than ninety percent of the failure load and less than or equal to ninety-nine percent of the failure load.

16. The system of claim 14, wherein the testing device includes a first element to secure the test coupon and a second element to secure the test coupon, wherein the first element of the testing device includes a first friction pad to secure directly and intimately to a first end of the test coupon, and wherein the second element of the testing device includes a second friction pad to secure directly and intimately to a second end of the test coupon, wherein the first element and the second element secure directly and intimately to the outermost ply layers having second fibers oriented in a nominal 90 degree direction.

17. The system of claim 14, wherein the first loading operation is separate and distinct from the second loading operation.

18. A system comprising:
a processor; and
a memory in communication with the processor, the memory including instructions executable by the processor to perform operations including:
   communicating with a testing device that is configured to perform load testing operations on a test coupon of a composite material having a plurality of layers, wherein the plurality of layers of the test coupon are arranged in a cross-ply layup including:
      inner ply layers having first fibers and a first matrix material associated with the first fibers, the first fibers oriented in a first direction; and
      outer ply layers having second fibers and a second matrix material associated with the second fibers, the outer ply layers including outermost ply layers and the second fibers oriented in a second direction that is different than the first direction;
   sending a first set of instructions to the testing device to perform a first loading operation on the test coupon, wherein the first loading operation includes applying a first tensile load oriented in the first direction, the first tensile load corresponding to a threshold load that is less than a failure load of the first fibers;
   removing the first tensile load after the first tensile load causes cracking along the second direction and between the second fibers of each of the outermost ply layers, the removing including causing a magnitude of the first tensile load to be zero;
   after removing the first tensile load, sending a second set of instructions to the testing device to perform a second loading operation on the test coupon, wherein the second loading operation includes increasing tensile loading of the test coupon to the failure load of the first fibers; and
   calculating one or more tensile strength values associated with a first contribution corresponding to the inner ply layers based on a nominal thickness of a ply area associated with the inner ply layers, the first contribution independent of a second contribution associated with the outer ply layers.

* * * * *